(12) United States Patent
Auer et al.

(10) Patent No.: US 6,284,541 B1
(45) Date of Patent: Sep. 4, 2001

(54) POSITIVE-NEGATIVE SELECTION FOR HOMOLOGOUS RECOMBINATION

(75) Inventors: Johannes Auer, Penzberg; Raimund Sprenger, Weilheim; Konrad Honold, Penzberg, all of (DE)

(73) Assignee: Roche Diagnostics GmbH, Mannheim (DE)

( * ) Notice: Subject to any disclaimer, the term of this patent is extended or adjusted under 35 U.S.C. 154(b) by 0 days.

(21) Appl. No.: 09/509,560

(22) PCT Filed: Oct. 20, 1998

(86) PCT No.: PCT/EP98/06616

§ 371 Date: Jun. 9, 2000

§ 102(e) Date: Jun. 9, 2000

(87) PCT Pub. No.: WO99/20780

PCT Pub. Date: Apr. 29, 1999

(30) Foreign Application Priority Data

Oct. 20, 1997 (EP) .................................................. 97118175

(51) Int. Cl.⁷ .......................... C12N 15/63; C12N 15/00; C12N 15/82; C12N 15/74
(52) U.S. Cl. ...................... 435/463; 435/320.1; 435/468; 435/477
(58) Field of Search .................. 435/320.1, 471, 435/455, 468, 463, 477

(56) References Cited

U.S. PATENT DOCUMENTS

| 5,464,764 | 11/1995 | Capecchi et al. ........................ 435/6 |
| 5,633,161 | * 5/1997 | Shyjan ................................. 435/325 |
| 5,641,670 | * 6/1997 | Treco et al. ........................ 435/240.2 |
| 5,721,351 | * 2/1998 | Levinson ............................ 536/23.4 |
| 6,074,836 | 6/2000 | Bordignon et al. ................. 435/7.24 |

FOREIGN PATENT DOCUMENTS

| 0 455 460 | 11/1991 | (EP) . |
| 92 09631 | 6/1992 | (WO) . |
| 94 29436 | 12/1994 | (WO) . |
| 95 06723 | 3/1995 | (WO) . |
| 97 08186 | 3/1997 | (WO) . |

OTHER PUBLICATIONS

Medin et al., "viral vectors for gene therapy of hematopoietic cells", Immunotechnology, vol. 3, Mar. 1997, pp. 3–19.
Database WPI, Section Ch, Week 8939, Derwent Publications Ltd., London, GB, JP 01 203975.

* cited by examiner

Primary Examiner—James Ketter
Assistant Examiner—Lisa Gansheroff
(74) Attorney, Agent, or Firm—Arent Fox Kintner Plotkin Kahn PLLC.

(57) ABSTRACT

The invention concerns a method for the introduction of a foreign DNA into the genome of a target cell by homologous recombination as well as for the homologous recombination of suitable DNA constructs.

32 Claims, 5 Drawing Sheets

Figure 1:
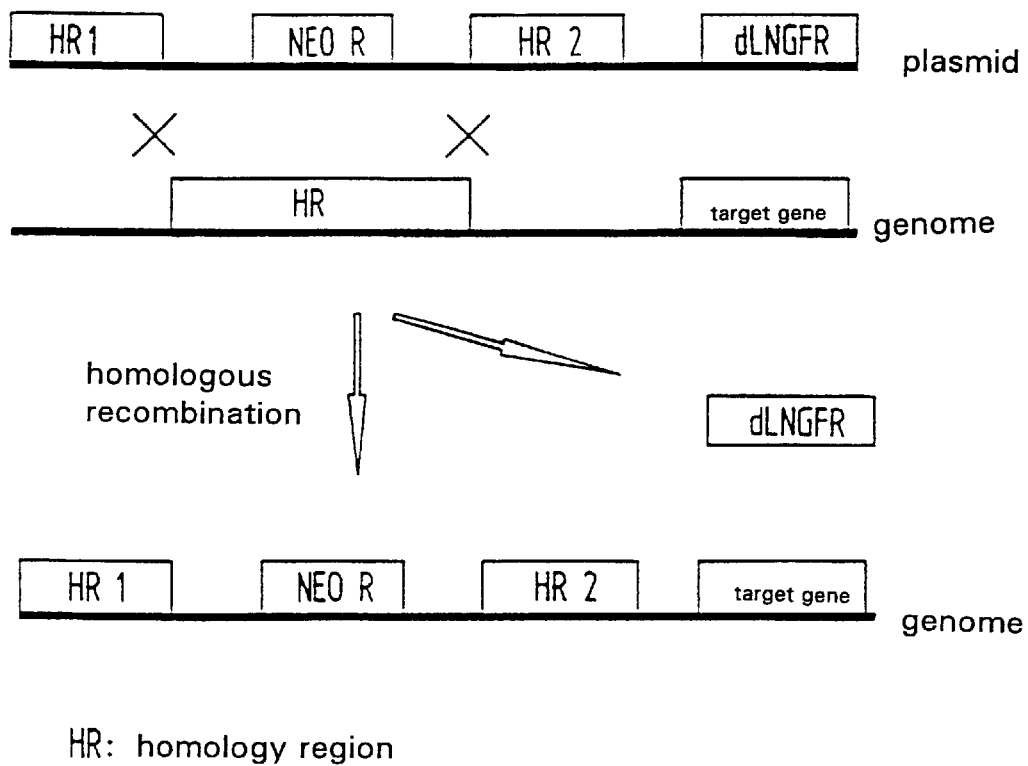

Principle of homologous recombination under negative selection by ΔLNGFR

Restriction map of the plasmid pSV-DLNGFR not transfected cells transfected cells
(2 days after transfection)

Restriction map of the plasmid 'p187-DLNGFR'.

Histogram statistics

Sample ID: Ht-1080, 2µg LNGFR transf.
X Parameter. FL1-H m<LNGFR>,gam IgG-FITC (Log)

| Marker | Left, Right | Events | % Gated | % Total | Mean | Geo Mean | CV | Median | Peak Ch |
|---|---|---|---|---|---|---|---|---|---|
| All | 1, 9910 | 13204 | 100.00 | 66.02 | 133.03 | 87.15 | 75.53 | 114.44 | 126 |
| M1 | 2, 24 | 1971 | 14.93 | 9.85 | 10.54 | 9.29 | 47.62 | 10.00 | 13 |

POSITIVE-NEGATIVE SELECTION FOR HOMOLOGOUS RECOMBINATION

DESCRIPTION

The invention concerns a method for introducing a foreign DNA into the genome of a target cell by homologous recombination as well as suitable DNA constructs for the homologous recombination.

Methods for introducing foreign DNA into the genome of eukaryotic cells by homologous recombination are known (e.g. WO 90/11354, WO 91/09955). In this process a starting cell is transfected with a DNA construct which contains at least one and preferably two DNA sequence sections that are homologous to regions of the genome of the cell to be transfected, a positive selection marker gene and optionally a negative selection marker gene. In addition the DNA construct can contain a heterologous expression control sequence if it is intended to activate a gene which is normally silent in the transfected cell. The transfected cells are cultured under conditions in which a selection for the presence of the positive selection marker gene takes place which, on expression, leads to a selectable phenotype.

A second selection step is usually carried out in order to distinguish between cells in which a homologous recombination has taken place and cells in which the vector has only been randomly integrated into the genome of the host cell. For this a negative selection marker gene is used such as the HSV thymidine kinase gene (HSV-TK) which, when present, leads to the destruction of cells in the presence of a selection agent e.g. ganciclovir. In homologous recombination the cell loses the HSV thymidine kinase gene so that cells are resistant to ganciclovir. Cells in the genome of which the targeting vector has been incorporated by random, non-homologous integration do not lose the HSV-TK gene and are therefore sensitive towards ganciclovir. Cells are preferably used for this type of selection by HSV-TK/ganciclovir which contain no functional thymidine kinase gene (e.g. CEM tk⁻ from Ogden Bioservices Corp., Rockville Md., USA, Cat. No. 491).

However, other host cells used for homologous recombination possess their own thymidine kinase gene. But this cellular thymidine kinase gene causes background problems in the negative selection. Thus for example homologously recombined clones may be lost during screening. Similar problems also occur with other negative selection marker genes which code for a gene product whose expression must be selected against after transfection.

The use of polypeptides located on the cell surface as positive transfection markers is known. Thus for example WO 95/06723 describes a method for labelling cells using a partially deleted cell surface receptor gene.

In order to avoid the problems which occur with the previously used negative selection marker genes, a negative selection marker gene is used according to the invention which codes for a polypeptide located on the cell surface.

Hence the present invention concerns a method for introducing foreign DNA into a host cell by homologous recombination in which the host cell is transfected with a recombinant vector comprising two flanking nucleotide sequences which are homologous to a target sequence in the genome of the host cell and inside of which a nucleotide sequence coding for a positive selection marker is located, and a nucleotide sequence outside the flanking sequences which codes for a negative selection marker, each of the nucleotide sequences coding for the positive and the negative selection marker being operatively linked to an expression control sequence which is active in the host cell, wherein at least one nucleotide sequence coding for a polypeptide located on the cell surface is used as the negative selection marker gene so that after integration of the DNA construct into the genome of the cell by homologous recombination the negative selection marker gene is not expressed and after a random integration of the vector into the genome of the cell the negative selection marker gene is expressed and its gene product is presented on the cell surface.

Hence according to the invention a negative selection marker gene coding for a polypeptide located on the surface is used for the homologous recombination at an appropriate site in the vector to avoid using a negative selection method with a selection agent that is toxic for the cell. A negative selection marker gene is preferably used which codes for a polypeptide which does not normally occur in the host cell.

Problems with toxicity or with background signals that have been described for TK selection do not occur in the method according to the invention. A further advantage of the method according to the invention is that the number of transfected cells that have to be examined for expression of the target gene is considerably reduced.

The host cell is preferably a eukaryotic cell, particularly preferably a mammalian cell and most preferably a human cell.

In order to identify and isolate cells in which a homologous recombination has taken place, a selection step is carried out according to the invention for the presence of the positive selection marker gene and a further selection step is carried out for the absence of the negative selection marker gene.

The selection step for the presence of the positive selection marker gene can be carried out in a conventional manner. Any selection marker gene, and especially those suitable for eukaryotic cells, whose expression results in a selectable phenotype e.g. antibiotic resistance or auxotrophy can be used as the positive selection marker gene. Antibiotic resistance genes are preferably used e.g. the neomycin, kanamycin, geneticin or hygromycin resistance gene. A particularly preferred positive selection marker gene is the neomycin phosphotransferase gene.

The negative selection marker gene used for the method according to the invention codes for a gene product which is presented on the surface of the host cell, preferably for a membrane-based polypeptide. Preferred examples of such membrane-based polypeptides are the LNGF, the CD24, the LDL or the trk receptor or a membrane-based receptor fragment containing the ligand binding domain of the respective receptor. Suitable receptor fragments in which the intracellular domain is completely or partially deleted or is modified in such a manner that the receptor presented on the surface cannot cause signal transduction are described in WO 95/06723. A particularly preferred example of such a receptor fragment is a deletion mutant of the LNGF receptor (dLNGFR) which is a fragment of the human low-affinity receptor of the nerve growth factor whose intracellular and signal transducing domains have been deleted (WO 95/06723).

The principle of homologous recombination under negative selection by dLNGFR is shown schematically in FIG. 1. This selection principle can of course be applied to other selection marker genes coding for surface-associated polypeptides. A plasmid is used as the recombinant vector which contains two flanking nucleic acid sections (HR1, HR2) homologous to the desired target sequence and between them the positive selection marker gene, the neomycin resistance gene (NeoR). A nucleotide sequence coding for dLNGFR is arranged on the plasmid outside the two flanking homologous nucleotide sequences.

The regions HR1, NeoR and HR2 are integrated into the genome when a homologous recombination occurs with a region in the area of the target gene (HR). However, the sequence coding for dLNGFR is not integrated into the genome. In contrast the dLNGFR gene is retained in a form capable of expression when the plasmid is randomly integrated into the genome of the host cell.

The selection according to the invention for the absence of the negative selection marker gene in the transfected host cell preferably comprises the steps:

(a) contacting the transfected cell with a binding molecule which binds to the gene product of the negative selection marker gene and (b) separating the cells containing the bound binding molecule.

Substances are used as binding molecules which can bind specifically and preferably with high affinity to the negative selection marker. Preferably those binding molecules are used which do not have any interfering cross-reactivity with other surface components of the an host cell. Examples of binding molecules are antibodies e.g. polyclonal or monoclonal antibodies, antibody fragments etc. which are directed against the gene product of the negative selection marker gene. Suitable antibodies to dLNGFR are for example known from WO 95/06723. When a receptor is used as a negative selection marker, a natural binding partner of the receptor, e.g. the receptor ligand or an analogue thereof, can of course also be used as a binding molecule. An example of such a receptor ligand is NGF as a ligand of LNGFR.

In order to facilitate the separation of the cells labelled with the negative selection marker, it is possible to use a binding molecule which is coupled to a solid phase and this coupling can be achieved by adsorption, covalent binding or by a high-affinity binding pair (e.g. streptavidin/biotin). The type of solid phase is generally uncritical for the method according to the invention and preferably those solid phases are used which enable an easy separation of the cells presenting the negative selection marker from unlabelled cells. Therefore the solid phase can be for example present in the form of a chromatographic column, but particulate solid phases such as microbeads, in particular magnetic microbeads, which enable a particularly simple separation are especially preferred.

Alternatively the transfected cells can also be contacted with free binding molecules. In this case the free binding molecules preferably carry a marker or/and a solid phase binding group. Examples for suitable marker or/and solid phase binding groups are biotin, biotin derivatives, e.g. iminobiotin, aminobiotin or desthiobiotin, haptens, e.g. digoxigenin, fluorescein, enzymes e.g. peroxidase or alkaline phosphatase or dyes e.g. fluorescent dyes such as fluorescein, phycoerythrin, rhodamine, peridinine-chlorophyl protein, Texas red or derivatives thereof.

If a binding molecule is used which carries a solid phase binding group such as biotin, a biotin derivative or a hapten, the cells labelled with the binding molecule can be coupled to a solid phase that can react with the solid phase binding group of the binding molecule. If a binding molecule is used which carries a biotin group, one can for example identify the cells expressing the negative selection marker and separate them from unlabelled cells by binding to an avidin or streptavidin-coated solid phase.

If a binding molecule is used which carries an enzymatic marker group, the cells expressing the negative selection marker can be identified after addition of an enzyme substrate by an enzyme catalysed color reaction and optionally separated from unlabelled cells. This identification can for example be carried out by putting the cells on a slide and subsequently analysing them microscopically.

If a binding molecule is used which carries a fluorescent dye, the cells expressing the negative selection marker can be identified by flow cytometric analysis and separated from unlabelled cells. This separation procedure is rapid and simple and can be carried out in conventional FACS instruments that enable the setting of fluorescence windows and cell sorting.

A further subject matter of the present invention is a recombinant vector which is suitable for use as a transfection vector in the method according to the invention. This vector comprises:

(a) two flanking nucleotide sequences that are homologous to a target sequence in a cell, (b) a nucleotide sequence coding for a positive selection marker under the control of an expression control sequence that is active in the cell and which is located inside of the two flanking sequences according to (a), (c) a nucleotide sequence coding for a negative selection marker under the control of an expression control sequence that is active in the cell which is located outside the flanking homologous nucleotide sequences and whose expression product is a polypeptide located on the cell surface.

If it is intended to use the recombinant vector to activate an endogenous gene in the host cell, it contains an additional heterologous expression control sequence which is active in the host cell between the two flanking homologous nucleotide sequences. This expression control sequence comprises a promoter and preferably further expression-improving sequences e.g. an enhancer. The promoter can be a regulatable or a constitutive promoter. The promoter is preferably a strong viral promoter e.g. an SV40 or a CMV promoter. The CMV promoter/enhancer is particularly preferred.

If an amplification of the target gene in the transfected host cell is desired, the recombinant vector contains an amplification gene between the two flanking sequences. Examples of suitable amplification genes are dihydrofolate reductase, adenosine deaminase, ornithine decarboxylase etc. A particularly preferred amplification gene is the dihydrofolate reductase gene, in particular a gene coding for a dihydrofolate reductase arginine mutant which has a lower sensitivity towards the selective agent (methotrexate) than the wild type polypeptide (Simonsen et al., Proc. Natl. Acad. Sci. USA 80 (1983), 2495).

The nucleotide sequence coding for the negative selection marker can—as elucidated above—preferably be selected from membrane-based receptors or membrane-based receptor fragments containing the ligand binding domain of the respective receptor.

The flanking nucleotide sequences that are homologous to a target sequence can be selected from any chromosomal regions of the genome of the cell to be transfected which is preferably a eukaryotic cell, particularly preferably a mammalian cell and most preferably a human cell. In the case of human cells the flanking homologous nucleotide sequences are preferably derived from the region of genes for human factors e.g. EPO, tPA, G-CSF, GM-CSF, TPO, interleukins, interferons, growth factors, insulin, insulin-like growth factor etc.

The flanking homologous nucleotide sequences can include the coding region of the target gene or a part thereof.

In this part they can be selected such that in a homologous recombination they cause a mutation in the coding region of the mature target polypeptide compared to the endogenous sequence present in the cell. This mutation can comprise substitutions, deletions and insertions of individual amino acids or whole amino acid sections.

Yet a further subject matter of the present invention is the use of membrane-based surface receptors as negative selection markers in a method of homologous recombination.

The invention is further elucidated by the following examples and figures.

Figure 2:
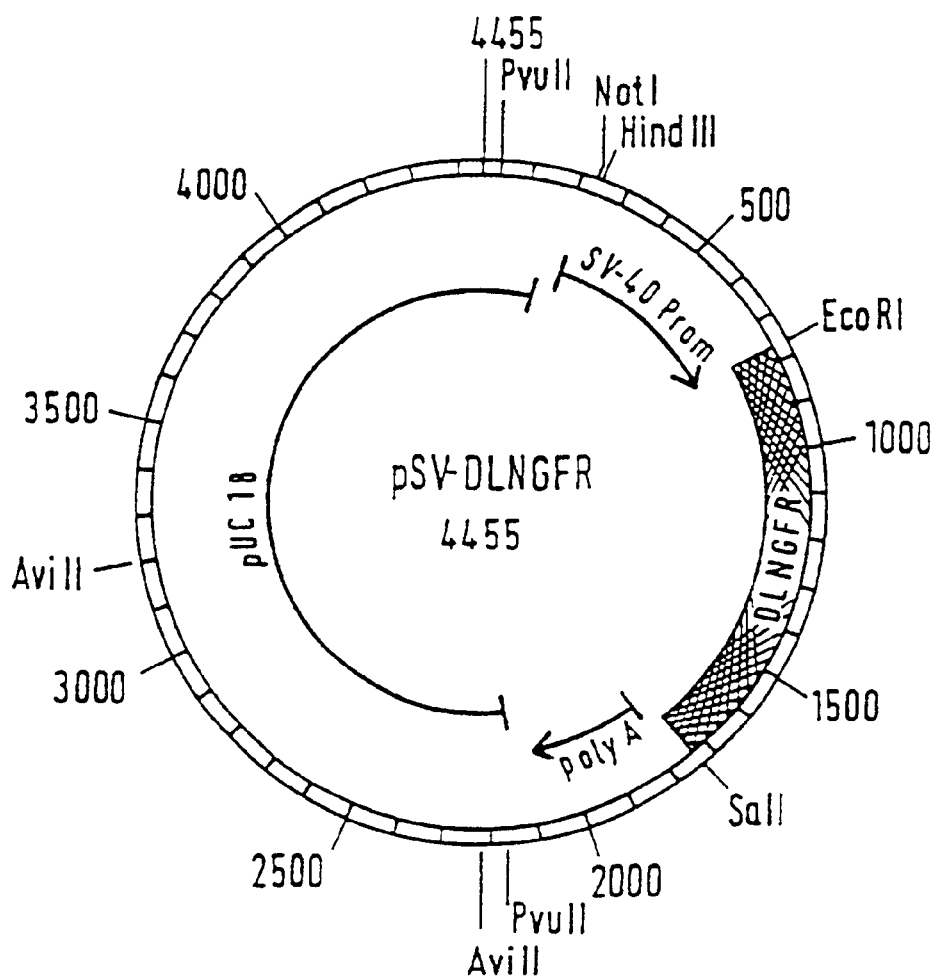
Figure 3A:
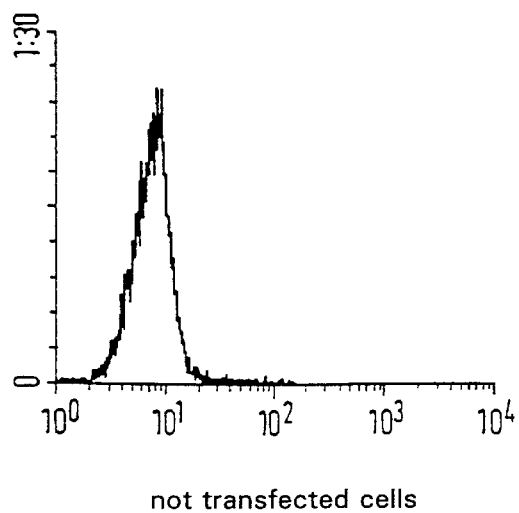
Figure 3B:
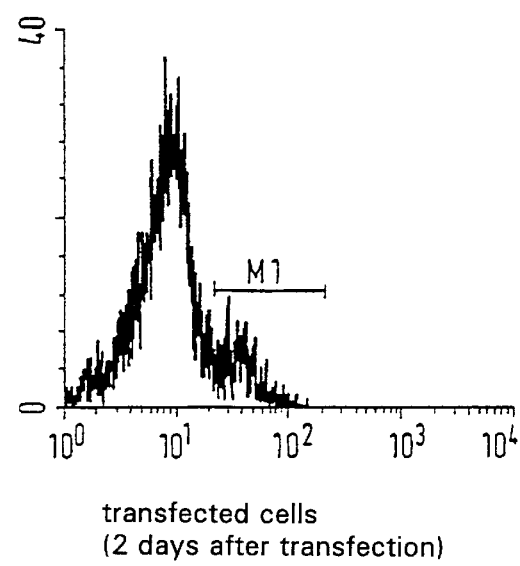
Figure 4:
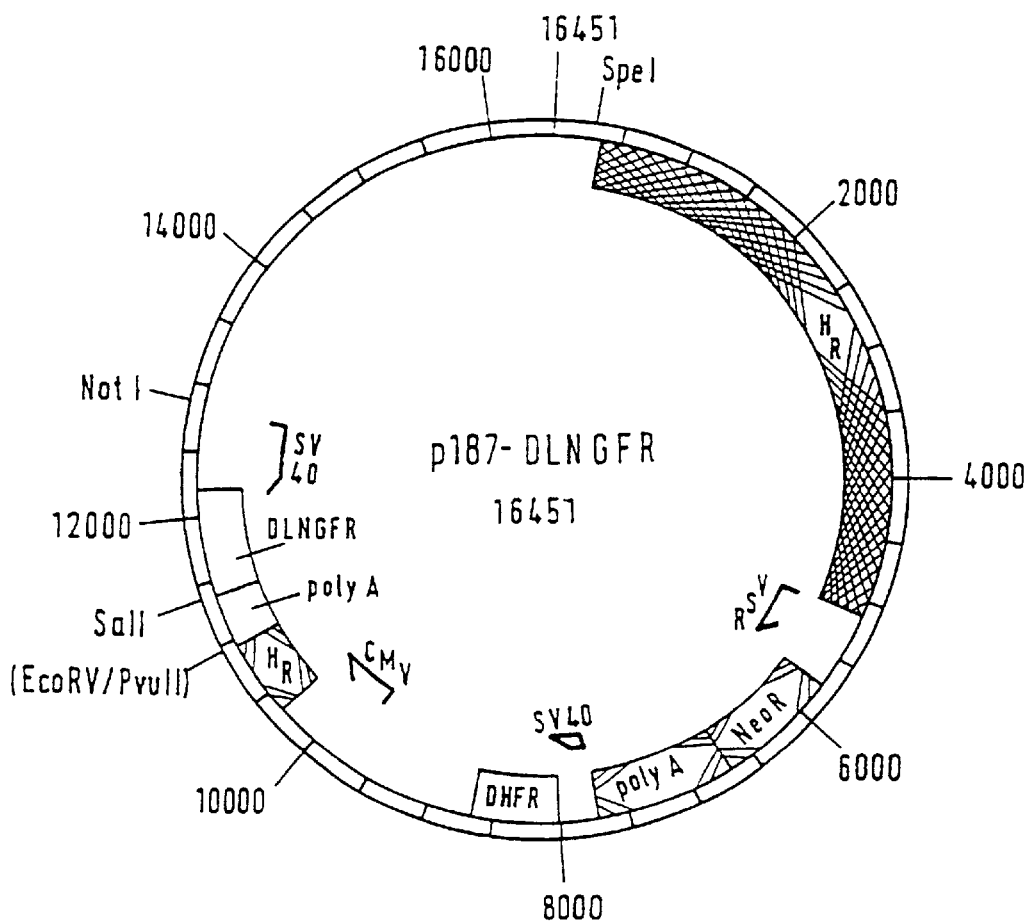
Figure 5:
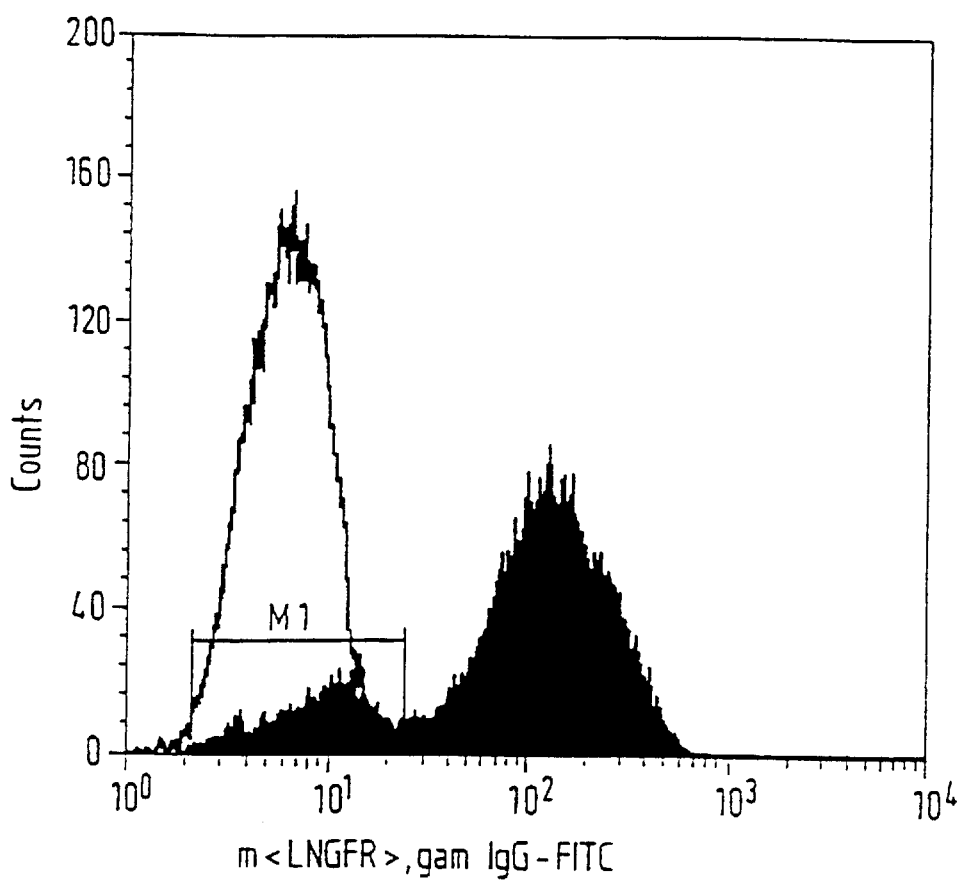

FIG. 1: shows a schematic representation of the principle of homologous recombination using a negative selection by dLNGFR according to the invention, FIG. 2: shows the restriction map of the plasmid pSV-dLNGFR, FIGS. 3a and 3b: show results of an FACS analysis of dLNGFR-expressing and non-expressing cells, FIG. 4: shows the restriction map of the plasmid p187-dLNGFR, FIG. 5: shows the result of an FACS analysis to differentiate between dLNGFR negative and positive cells.

EXAMPLES

Methods

Recombinant DNA Technique

Standard methods were used for the manipulation of DNA as described in Sambrook, J. et al. (1989) in: Molecular Cloning: A Laboratory Manual, Cold Spring Harbor Laboratory Press, Cold Spring Harbor, N.Y. The molecular biological reagents were used according to the manufacturer s instructions.

Transfection of Human Cell Lines, Cultivation and Cloning

The vector was present dissolved at a concentration of 1 µg/µl double distilled water. In order to ensure a high transfection efficiency, the cells were transfected with the aid of electroporation (BioRad, Genepulser™) under conditions that were-previously determined to be optimal (960 µF/260 MV/18–22 µS). The adherently growing human fibrosarcoma line HT1080 (ATCC CCL 121) was used as a suitable cell line at a concentration of $10^7$ cells/0.8 ml. The cells were kept for ca. 10 min on ice before and after transfection in order to reconstitute the cell membrane.

Transfected cells were sown in T-175 culture flasks and cultured in an incubator at 37° C. and 7% $CO_2$. After 24 h selection pressure was applied by adding G418 (0.8 µg/ml). After 14 days in culture resistant clones appeared in the culture dish. After larger foci had grown, the cells were washed with PBS, trypsinized and stained as single cell suspension.

FACS Analysis

The staining steps were carried out on ice using $10^5$ cells/preparation. The anti-dLNGFR antibody from the mouse used as the primary antibody was detected by adding a secondary antibody from the goat (a-mlgG-FITC, 1:25, Caltag). The cells were stained with the secondary antibody alone as a control for unspecific binding. Dead cells were detected by adding propidium iodide (10 µg/ml). The analyses were carried out on a FACS-Vantage (Becton Dickinson Co.) according to the manufacturer's instructions. The specific fluorescence of cells expressing dLNGFR was recorded in the FL-1 channel and the dead cells in the FL-3 channel.

Example 1

Preparation of the Expression Construct for dLNGFR

The gene for dLNGFR (WO 95/06723, Boehringer Mannheim GmbH) which comprises 965 bp was amplified with the aid of the PCR method. The primers used introduced cleavage sites for the enzymes EcoRI and SalI at both ends. After amplification the PCR fragments were cleaved with both enzymes.

The vector pSV1 which contains the early SV40 promotor and the SV40 polyA-signal (Okayama and Berg, Mol.Cell.Biol.3 (1983), 280–289; Muligan and Berg, Proc. Natl. Acad. Sci. USA 78 (1981), 2072–2076) was also cleaved with EcoRI and SalI.

The isolated vector has a size of 3490 bp. The dLNGFR fragment is ligated into the vector pSV1. The gene for dLNGFR was under the expression control of the early SV40 promoter and the SV40 poly-signal. The entire expression cassette comprises 1900 bp. The resulting vector PSV-DLNGR is shown in FIG. 2.

Example 2

Testing the Expression Cassette for Functionality

Cells of the line HT1080 were transiently transfected with the plasmid pSV-DLNGFR as described above. After two days growth the cells were analysed for expression of dLNGFR with the aid of the monoclonal anti-dLNGFR antibody. The result is shown in FIG. 3 which shows that dLNGFR-expressing and non-expressing cells can be distinguished by FACS analysis. It also shows that the reaction of the anti-dLNGFR antibody is specific for transfected cells.

Example 3

Cloning the dLNGFR Expression Cassette Into a Gene Targeting Vector

The dLNGFR expression cassette was isolated from pSV-DLNGFR using the restriction enzymes NotI and PvuII. The targeting vector 'p187' for the human EPO-gene (described in EP 97 112 649.5 and EP 97 112 640.5 see FIG. 4b) was cleaved with NotI and EcoRV. The 14551 bp large vector fragment was isolated and ligated with the dLNGFR expression cassette (FIG. 4). The resulting plasmid 'p187-DLNGFR' was transferred into E.coli and propagated therein.

Example 4

Test for Negative Selection in the FACS Scan

HT1080 cells were transfected with p187-DLNGFR and selected for stable integration i.e. G418 was added to the medium 24 hours after transfection. The first FACS analysis was carried out after ca. 3 weeks growth and namely after formation of the first foci whose cells were pooled. As shown in FIG. 5 dLNGFR negative cells, in this case 14% of the population, can at this time be distinguished from the dLNGFR-expressing cells by FACS analysis.

In addition to the rarely occurring event of homologous recombination this cell population, also contains cells whose surface receptor density is too low and therefore are not recognized by the detection system. However, in this manner the number of clones which have to be subsequently tested for the expression of the target gene can be considerably reduced (in this case 14 of 100%).

If in a transfection preparation no clone is present which contains a homologously recombined targeting vector, then this situation can be indicated with much less work compared to the conventional screening. The absence of homologously recombined clones is demonstrated by the occurrence of a population reacting 100% with anti-dLNGFR antibodies. In this case it is not necessary to screen further for the expression of target gene.

What is claimed is:

1. A method for introducing foreign DNA into a host cell by homologous recombination, comprising transfecting the host cell with a recombinant vector comprising:
   a) two flanking nucleotide sequences which are homologous to a target gene sequence in the genome of the host cell,
   b) a nucleotide sequence encoding a positive selection marker located between the two flanking nucleotide sequences,
   c) nucleotide sequence encoding a negative selection marker located outside the two flanking sequences, and
   d) each of b) and c) are operatively linked to an expression control sequence which is active in the host cell,
      wherein the negative selection marker comprises at least one nucleotide sequence encoding a polypeptide located on the cell surface, and wherein the negative selection marker is not expressed after a targeted integration of the vector into the genome of the cell by homologous recombination, and is expressed and presented on the cell surface after a random integration of the vector into the genome of the cell.

2. The method as claimed in claim 1, wherein a selection step combines detecting the expression of the positive selection marker and the negative selection marker.

3. The method as claimed in claim 2, wherein detecting the expression of the negative selection marker comprises the steps of:
   (a) contacting a transfected cell with a binding molecule which binds to the polypeptide located on the cell surface; and
   (b) identifying the transfected cell having a bound binding molecule, and
      wherein the cells containing the bound binding molecule are separated from cells without a bound binding molecule.

4. The method as claimed in claim 3, wherein the binding molecule is an antibody.

5. The method as claimed in claim 3, wherein the binding molecule is a ligand.

6. The method as claimed in claim 3, wherein the binding molecule is coupled to a solid phase.

7. The method as claimed in claim 6, wherein the solid phase is a magnetic microbead.

8. The method as claimed in claim 3, wherein the binding molecule is conjugated to a marker and/or a solid phase binding group.

9. The method as claimed in claim 8, wherein the marker and/or the solid phase binding group is selected from the group consisting of a biotin molecule, a biotin derivative, a hapten, an enzyme and a dye.

10. The method as claimed in claim 9, wherein the marker, solid phase binding group, or a combination thereof, is selected from the group consisting of biotin, iminobiotin, aminobiotin and desthiobiotin.

11. The method as claimed in claim 10, wherein the biotin molecule or the biotin derivative is detected by binding to an avidin or a streptavidin-coated solid phase.

12. The method as claimed in claim 9, wherein the enzyme is an alkaline phosphatase or a peroxidase.

13. The method as claimed in claim 12, wherein the enzyme is identified by an enzyme-catalyzed color reaction.

14. The method as claimed in claim 9, wherein the dye is a fluorescent dye.

15. The method as claimed in claim 14, wherein the fluorescent dye is fluorescein, phycoerythrin, rhodamine, peridininechlorophyl protein or Texas red.

16. The method as claimed in claim 14, comprising detecting the dye or the fluorescent dye by flow-cytometric analysis.

17. The method as claimed in claim 1, wherein the cell is a eukaryotic cell.

18. The method according to claim 17, wherein the cell is a mammalian cell.

19. The method according to claim 17 or 18, wherein the cell is a human cell.

20. The method as claimed in claim 1, wherein the nucleotide sequence for the negative selection marker encodes a receptor wherein the receptor is at least one of an LNGF receptor, a CD24 receptor, an LDL receptor, a trk receptor, and a membrane-based receptor or a fragment thereof, and wherein said receptor or fragment thereof encoded by the negative selection marker comprises a domain for binding extracellular ligands.

21. A recombinant vector comprising
   a) two flanking nucleotide sequences that are homologous to a target gene sequence in a cell,
   b) a nucleotide sequence encoding a positive selection marker under the control of an expression control sequence that is active in the cell, wherein the nucleotide sequence is located inside of the two flanking sequences according to (a), and
   c) a nucleotide sequence encoding a negative selection marker under the control of an expression control sequence that is active in the cell, wherein the nucleotide sequence of c) is located outside the flanking homologous nucleotide sequences according to (a), and an expression product of the nucleotide is a polypeptide located on the cell surface.

22. The vector as claimed in claim 21, wherein the two flanking nucleotide sequences which contain the target gene sequence are selected from the group consisting of EPO, tPA, G-CSF, GM-CSF, thrombopoietin, an interleukin, an interferon, a growth factor, insulin or insulin-like growth factor.

23. The vector as claimed in claim 21, wherein the nucleotide sequence encoding the positive selection marker is a drug-resistance gene selected from the group consisting of neomycin, kanamycin, geneticin and hygromycin.

24. The vector as claimed in claim 21, wherein a further expression control sequence is located inside of the flanking sequences.

25. The vector as claimed in claim 24, wherein the expression control sequence comprises a CMV promoter.

26. The vector as claimed in claim 21, further comprising an amplification sequence positioned inside of the flanking sequences.

27. The vector as claimed in claim 21, wherein the two flanking nucleotide sequences contain the coding region of the target gene or a part thereof.

28. The vector as claimed in claim 27, wherein the two flanking nucleotide sequences are sequences for introducing a mutation within the coding region of the nucleotide sequence encoding the mature target polypeptide by homologous recombination.

29. The vector as claimed in claim 21, wherein the nucleotide sequence encoding the negative selection marker encodes a membrane-based molecule selected from the group consisting of a LNGF receptor, a CD24 receptor, a LDL receptor, a trk receptor, and a membrane-based receptor or a fragment thereof, and wherein the membrane-based molecule encoded by the negative selection marker comprises a domain for binding extracellular ligands.

30. A recombinant vector comprising
   a) two flanking nucleotide sequences that are homologous to a target gene sequence in a cell,
   b) a nucleotide sequence encoding a positive selection marker under the control of an expression control sequence that is active in the cell, wherein the nucleotide sequence is located inside of the two flanking sequences according to (a), and
   c) a nucleotide sequence encoding a negative selection marker under the control of an expression control sequence that is active in the cell, wherein the nucleotide sequence of c) is located outside the flanking homologous nucleotide sequences according to (a), and an expression product of the nucleotide sequence is a receptor fragment containing an extracellular ligand binding domain and located on the cell surface, with the proviso that an intracellular domain of the receptor fragment is fully or partially deleted or modified, and wherein by deleting or modifying said intracellular domain of said receptor fragment, said receptor fragment is incapable of signal transduction.

31. A method for endogenous gene activation comprising introducing foreign DNA into a host cell by homologous recombination, comprising transfecting the host cell with a recombinant vector comprising:
   a) two flanking nucleotide sequences which are homologous to a target gene sequence in the genome of the host cell,
   b) a nucleotide sequence encoding a positive selection marker located between the two flanking nucleotide sequences,
   c) a nucleotide sequence encoding a negative selection marker located outside the two flanking sequences, and
   d) each of b) and c) are operatively linked to a heterologous expression control sequence which is active in the host cell, and
   e) an additional heterologous expression control sequence which is active in the host cell, and which is between the two flanking homologous nucleotide sequences,
      wherein the negative selection marker comprises at least one nucleotide sequence encoding a polypeptide located on the cell surface, and wherein the negative selection marker is not expressed after a targeted integration of the vector into the genome of the cell by homologous recombination and is expressed and presented on the cell surface after a random integration of the vector into the genome of the cell.

32. The method according to claim 31, wherein the heterologous expression control sequence of e) is a regulatable promoter or a constitutive promoter.

* * * * *